(12) United States Patent
Simon et al.

(10) Patent No.: US 7,514,071 B2
(45) Date of Patent: Apr. 7, 2009

(54) SINGLE-USE COSMETIC ARTICLE

(75) Inventors: Pascal Simon, Thiais (FR);
Anne-Clotilde Chaboussant-Roche, Paris (FR)

(73) Assignee: L'Oreal S.A., Paris (FR)

( * ) Notice: Subject to any disclaimer, the term of this patent is extended or adjusted under 35 U.S.C. 154(b) by 722 days.

(21) Appl. No.: 11/074,056

(22) Filed: Mar. 8, 2005

(65) Prior Publication Data
US 2005/0238698 A1  Oct. 27, 2005

Related U.S. Application Data

(60) Provisional application No. 60/553,129, filed on Mar. 16, 2004.

(30) Foreign Application Priority Data
Mar. 8, 2004  (FR) .................................. 04 50469

(51) Int. Cl.
*A61Q 1/10* (2006.01)
*A61K 8/02* (2006.01)
(52) U.S. Cl. ........................................ 424/69; 424/401
(58) Field of Classification Search .................. 424/69, 424/401
See application file for complete search history.

(56) References Cited

U.S. PATENT DOCUMENTS

| | | | |
|---|---|---|---|
| 4,948,585 A | | 8/1990 | Schlein |
| 5,620,694 A | | 4/1997 | Girardot |
| 6,042,844 A | | 3/2000 | Ishida et al. |
| 6,440,437 B1 * | | 8/2002 | Krzysik et al. .............. 424/402 |
| 6,753,063 B1 * | | 6/2004 | Pung et al. .................. 428/152 |
| 2002/0155772 A1 * | | 10/2002 | Wong et al. ................. 442/123 |
| 2003/0215486 A1 * | | 11/2003 | Berry et al. ................. 424/443 |
| 2007/0082032 A1 * | | 4/2007 | Gregoire et al. ............. 424/443 |

FOREIGN PATENT DOCUMENTS

| | | |
|---|---|---|
| EP | 0 750 062 A1 | 12/1996 |
| EP | 1 066 826 B1 | 1/2001 |
| EP | 1 264 561 A1 | 12/2002 |
| EP | 1 352 950 A2 | 10/2003 |
| FR | 2 858 225 | 2/2005 |
| JP | 2-295912 | 12/1990 |
| WO | WO 99/25318 | 5/1999 |
| WO | WO 03/043551 A1 | 5/2003 |

OTHER PUBLICATIONS

Search performed for centipoise=mPas, [online], [retrieved on Mar. 24, 2008], Retrieved from the Internet:<URL:http://encyclopedia.farlex.com/centipoise>.*
Th. Förster et al., "Phase Inversion Emulsification," Cosmetics & Toiletries, vol. 106, Dec. 1991, pp. 49-52.
Takeo Mitsui et al., "Application of the phase-inversion-temperature method to the emulsification of cosmetics," American Cosmetics and Perfumery, vol. 87, 1972, pp. 33-36.
English language Derwent Abstract of EP 1 264 561, Dec. 11, 2002.
English language Derwent Abstract of FR 2 858 225, Feb. 4, 2005.
English language Derwent Abstract of JP 2-295912, Dec. 6, 1990.

* cited by examiner

*Primary Examiner*—Raymond J Henley, III
(74) *Attorney, Agent, or Firm*—Finnengan, Henderson, Farabow, Garrett & Dunner, L.L.P.

(57) ABSTRACT

The present patent application relates to a single-use cosmetic article containing a water-insoluble substrate impregnated with an aqueous cosmetic composition, said substrate being permeable and containing at least a first group of fibers and at least a second group of fibers whose hydrophilicity is different from that of the fibers of the first group. The first and second groups of fibers are arranged such that a first face of the substrate has a hydrophilicity substantially greater than the hydrophilicity of a second face of the substrate, opposite the first face.

28 Claims, No Drawings

SINGLE-USE COSMETIC ARTICLE

This application claims benefit of U.S. Provisional Application No. 60/553,129, filed Mar. 16, 2004, of French Application No. 04/50469, filed Mar. 8, 2004, both of which are herein incorporated by reference.

The present disclosure relates to a single-use article impregnated with a cosmetic composition.

Cosmetic articles such as disposable preimpregnated wipes are well known for their practical nature. These wipes consist of a sheet of water-insoluble substrate, generally a nonwoven, impregnated with a liquid cosmetic composition. The nonwoven is cut into a format suitable for a single use and impregnated with the necessary dose of cosmetic product.

When packaged in flexible packets that may contain from several articles to several dozen articles, they may be readily transported and used almost anywhere. As they are made of nonwovens, they may be readily produced industrially at acceptable costs, and in varied shapes best suited to their use.

The nonwoven substrate used in wipes is generally a fibrous network, the fiber density and composition of which is homogeneous throughout its thickness, and the two faces of the substrate of which consequently have the same fiber composition. The fibers used are generally mixtures of hydrophobic fibers, which are mostly made of polypropylene or terephthalate polyester, and hydrophilic fibers, which are mostly cellulose-based, for instance cotton or viscose. The cosmetic composition is uniformly impregnated throughout the thickness of the substrate, and, during the use of the wipe on the skin or the hair, the cosmetic composition is released in an equivalent and unpreferential manner through the two faces of the article.

Thus, when the user takes a wipe in her hand and passes it over her face, body or hair, its content is released as much on the hand as on the area to be treated. This may be perceived as a major defect, when compared to other more conventional modes of application. For example, in the field of makeup removal, a user impregnates only one face of a makeup-removing cotton-wool pad with makeup-removing milk and therefore does not soil her fingers during the makeup removal. This problem is particularly associated with products such as self-tanning products, skin-coloring products or hair-coloring products.

For this reason, an impregnating wipe whose substrate is capable of releasing its contents, for example, through one of its two faces, wherein the releasing face, may face the area to be treated, is desired.

Substrates impregnated on only one face are already known. These are multilayer substrates comprising an impermeable membrane fixed either onto a layer of a fibrous substrate or between two fibrous layers, wherein one of the substrates may be impregnated with a composition. Typically, the various layers are first manufactured separately and then assembled in a second step. For example, European Patent EP 1 066 826 describes a three-layer substrate comprising two outer fibrous sheets and a sandwiched impermeable thermoplastic film, wherein the completed article is assembled by means of heat-welding points. A first face of the substrate may serve, for example, to absorb the sebum present on the forehead and the nose, while the other face may be impregnated with an aqueous lotion that serves to refresh the skin.

Methods are also known for assembling an impermeable film onto an absorbent fibrous substrate via assembly techniques such as hot-bonding or by hot-coating.

The aforementioned solutions are not satisfactory however, because the multilayer substrates used may have high rigidity and tend to delaminate when they are impregnated with liquids containing oils, such as emulsions, or liquids containing glycols. As a result, the multilayer substrates are not pleasant to use.

In addition, the multi-step method for obtaining these multilayer substrates makes them more complicated to produce and more expensive than a substrate manufactured in a single step. The modes of "converting" (impregnation of the substrate, folding and packaging) are also more complex to perform, since they require coating techniques intended to selectively impregnate only one face, and the use of a specific method of folding.

In all the implementation examples of French patent application FR 03/09234, filed on Jul. 28, 2003, the most hydrophilic layer of the multilayer structure is arranged between two layers of fibers made of hydrophobic material. Therefore, the most hydrophilic layer cannot come into contact with the surface to be treated.

Thus, it would be desirable to produce a cosmetic article of the abovementioned type that makes it possible to solve all or some of the problems discussed above with reference to the conventional techniques. It would also be desirable to produce an article that is simple and economical to make, while also being practical and comfortable for use.

Other aspects and benefits of the present disclosure will become apparent upon reading the detailed description and the non-limiting examples below.

According to the present disclosure, at least one of the above-discussed problems of the prior art may be solved by making a single-use cosmetic article comprising a substrate impregnated with an aqueous liquid cosmetic composition, wherein the substrate is permeable and comprises at least a first and a second group of fibers, wherein the hydrophilicity of the second group of fibers is different from that of the fibers of the first group, the first and second groups of fibers being present within the same layer of the substrate and arranged such that a first face of the substrate has a hydrophilicity substantially greater than the hydrophilicity of a second face of the substrate, opposite the first face, the first face being external to the substrate.

Accordingly, the first face may be placed in contact with the surface to be treated, such as the skin or the hair.

In one non-limiting aspect of the present disclosure, the substrate comprises only one layer.

With such an article, the gain in efficacy of a cosmetic treatment may be substantially improved by allowing the release of larger amounts of the product with which the article is impregnated onto the surface to be treated.

Furthermore, the cleanliness of use of the article is improved, particularly in the case of self-tanning products, or skin- or hair-coloring products.

The cosmetic articles according to the present disclosure may also allow modes of application that are different from those of conventional wipes. Specifically, with the articles according to this disclosure, it is possible to apply the product to the area to be treated with the more hydrophilic face, and then to wipe off or efface the surplus with the less hydrophilic face.

In one non-limiting aspect of the disclosure, a single article may be used to perform two-step treatments. For example, the less hydrophilic face of the article, i.e., the face less liable to release the cosmetic product, may be used to exfoliate the skin, and then the other, softer face of the article may be used to release a large amount of the impregnated product onto the exfoliated skin. For example, the release of the impregnated product onto the exfoliated skin may be a soothing care treatment.

As used herein, the term "permeable" denotes a substrate capable of being traversed through its entire thickness by a cosmetic composition. Thus, unlike the aforementioned articles of the prior art discussed above, the article according of the present disclosure does not comprise an impermeable layer capable of forming a barrier to the composition with which it is impregnated.

In another non-limiting embodiment of the present disclosure, the substrate is insoluble in water, i.e., its integrity is not substantially affected by the presence of the aqueous cosmetic composition with which it is impregnated for at least the entire service life of the product.

The fact that the fibers of the first and second groups are arranged within the same layer of the substrate means that the two groups of fibers are linked together during the same linking process. However, the distribution of the two groups of fibers is non-homogenous throughout the thickness of the layer, and, according to one profile, may be characterized by:

- a majority of fibers of the first group on the first face of the layer;
- a majority of fibers of the second group on the second face of the layer, and, between the two faces,
- a relative amount of fibers of the first group that varies according to a relatively progressive profile, the slope of which is of opposite sign to that of the relatively progressive profile corresponding to the relative amount of fibers of the second group.

Such a structure differs from structures with separate layers in which various layers are formed and linked separately, and then bonded together by hot-bonding, hot-welding or by ultrasound.

In one non-limiting embodiment of the present disclosure, the first face of the substrate has a release index under static pressure (RISP1), and the second face of the substrate has a release index under static pressure (RISP2), such that the ratio RISP1/RISP2 is greater than or equal to 1.5.

Release Index Under Static Pressure (RISP):

The test below describes how to measure the release index under static pressure (RISP) of the two faces of an article impregnated with a cosmetic product as disclosed above. The RISP represents the amount of liquid impregnated in the support that may be released by each of the two faces of the support under the effect of static pressure. RISP also reveals whether there is a difference in release between the 2 faces.

When using the article, a consumer typically wipes her skin or hair with a first face of the article, the other face of the article being in contact with her hand. Therefore it is desirable to determine the amount of liquid simultaneously released by both faces of the support.

RISP is measured as follows: two sheets of absorbent material, such as a paper towel having the brand name WYPALL L30 (reference 7303) sold by Kimberley-Clark, with a basis weight of 50 g/m$^2$, are accurately weighed to the nearest hundredth of a gram, using a Mettler Toledo PR5002 balance. The sheets of absorbent material must be at least as large as the article to be tested, and, for example, slightly larger such that they overlap the outer edge of the support by at least two centimeters.

The first sheet of absorbent material is placed on a glass plate having dimensions at least as large as those of the article to be tested. The article to be tested is placed on the first sheet of absorbent material. The second sheet of absorbent material is then placed on top of the article to be tested.

A metal plate with a surface area at least equal to the surface area of the article to be tested, and weighing 3.7 kg, is placed on the assembly. After one minute, the plate is removed and each sheet of absorbent material is weighed.

The weight of liquid that has impregnated each sheet of absorbent material is calculated by subtracting the mass of a sheet of the absorbent material before the test from the mass of the same sheet of absorbent material after the test. The result of this calculation corresponds to the amount of liquid that was released from the face of the article with which the absorbent sheet was in contact. This result is represented as RISP1 for the face having higher hydrophilicity, and RISP2 for the face having lower hydrophilicity.

The ratio of RISP1 to RISP2 indicates the difference in release between the two faces of the wipe.

The value retained for the ratio RISP1/RISP2 is the mean value of measurements performed on four articles.

In a non-limiting embodiment of the present disclosure, the ratio RISP1/RISP2 ranges from 1.5 to 15, such as from 2.5 to 10, or from 2.5 to 7.

In another non-limiting embodiment of the present disclosure, the article may be in the shape of a glove formed from two sheets of the absorbent material. In this case, the ratio of RISP1/RISP2 is measured by separating the two sheets forming the glove, and measuring the RISP1 and RISP2 of the separated sheets.

Substrate

The substrate used for the above-described article may be manufactured according to water-jet bonding processes conventionally used for the preparation of nonwovens. The following is a non-limiting example of a process for making the articles of the present disclosure.

First, webs of fibers having different hydrophilicities are produced. These webs may be prepared according to various methods known to those skilled in the art, such as by carding using balls of fibers, by extrusion of polymer in the form of continuous filaments of fibers, or via an aero-pneumatic process.

The webs of fibers having different hydrophilicities (i.e., some that are more hydrophilic and some that are less hydrophilic) are placed on a conveyor belt and conveyed under arrays of jets of water at high pressure, which bind the fibers together. These high-pressure water jets cause rearrangement of the fibers in three directions within the fibrous structure, thus leading to overlapping of the fibers and binding them together without any addition of chemical binding agents. Generally, the webs of fibers are passed under several arrays of water jets whose pressure gradually increases from the first array to the last. This technique is known as hydrobonding.

Further, the substrate may be embossed, hemstitched, calendered or printed on, or may undergo any type of line-end treatment. Thus, one of the faces of the support, such as the less hydrophilic face, may be rendered exfoliant, for example, by hot-calendering.

According to the above-described process, it should be noted that, although formed from two webs of fibers, in the end the substrate comprises only one layer. As a result, the risks of delamination, observed in the above described multilayer articles of the prior art, may be eliminated.

The more hydrophilic fibers may be chosen, for example, from cotton, cellulose or viscose fibers.

The less hydrophilic fibers may be chosen from polypropylene, polyester, polyamide or polyethylene fibers. In one embodiment, the substrate may be impregnated with a cosmetic composition to a degree ranging from 100% to 1000%, such as from 150% to 800%, for example, from 150% to 400% by weight of composition relative to the weight of non-impregnated substrate.

Cosmetic Composition:

The cosmetic composition used according to the present disclosure to impregnate the water-insoluble substrate comprises a physiologically acceptable aqueous medium, i.e., a medium that is compatible with the skin, mucous membranes, the hair, and the scalp.

The liquid cosmetic composition may comprise from 10% to 99.9% of water, such as from 30% to 90% of water.

The compositions used according to the present disclosure may be in any galenical form that is suitable for topical application, such as in the form of an aqueous or aqueous-alcoholic solution, a homogeneous or two-phase lotion, a milk, an aqueous or aqueous-alcoholic gel, an emulsion obtained by dispersing a fatty phase in an aqueous phase (oil/water) or vice versa (water/oil), a suspension, a microemulsion, a microcapsule, a microparticle dispersion, and an ionic (liposome) or nonionic vesicular dispersion.

When the composition is an emulsion, the fatty phase may be present in a proportion of from 0.5% to 80% by weight, for example from 1% to 50% by weight relative to the total weight of the cosmetic composition.

The fatty or oily phase of the emulsion typically contains at least one oil. As oils that may be used in the composition of the present disclosure, mention may be made, for example, of:

hydrocarbon-based oils of animal origin, such as perhydrosqualene;

hydrocarbon-based oils of plant origin, such as liquid triglycerides of fatty acids containing from 4 to 10 carbon atoms, for instance heptanoic or octanoic acid triglycerides or alternatively, for example, sweet almond oil, sunflower oil, corn oil, soybean oil, marrow oil, grapeseed oil, sesame oil, hazelnut oil, apricot oil, macadamia oil, arara oil, sunflower oil, castor oil, avocado oil, caprylic/capric acid triglycerides, for instance those sold by the company Stearinerie Dubois or those sold under the names MIGLYOL 810, 812 and 818 by the company Dynamit Nobel, jojoba oil or shea butter oil;

synthetic esters and synthetic ethers, especially of fatty acids, for instance oils of formulae $R^1COOR^2$ and $R^1OR^2$ in which $R^1$ represents a fatty acid residue containing from 8 to 29 carbon atoms and $R^2$ represents a branched or unbranched hydrocarbon-based chain containing from 3 to 30 carbon atoms, such as, for example, purcellin oil, isononyl isononanoate, isopropyl myristate, isopropyl palmitate, 2-ethylhexyl palmitate (or octyl palmitate), 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate and fatty alkyl heptanoates, octanoates and decanoates; polyol esters, such as propylene glycol dioctanoate, neopentyl glycol diheptanoate and diethylene glycol diisononanoate; and pentaerythritol esters, for instance pentaerythrityl tetraisostearate;

linear or branched hydrocarbons of mineral or synthetic origin, such as volatile or non-volatile liquid paraffins, and derivatives thereof, petroleum jelly, polydecenes, and hydrogenated polyisobutene such as Parleam® oil;

fatty alcohols containing from 8 to 26 carbon atoms, for instance cetyl alcohol, stearyl alcohol and a mixture thereof (cetearyl alcohol), octyldodecanol, 2-butyloctanol, 2-hexyldecanol, 2-undecylpentadecanol, oleyl alcohol or linoleyl alcohol;

alkoxylated and especially ethoxylated fatty alcohols such as oleth-1 2 or ceteareth-20;

partially hydrocarbon-based and/or silicone-based fluoro oils, such as those described in document JPA2295912. Examples of fluoro oils which may also be mentioned include perfluoromethylcyclopentane and perfluoro-1, 3-dimethylcyclohexane, sold under the names "Flutec PC1®" and "Flutec PC3®" by the company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the company 3M, or alternatively bromoperfluorooctyl sold under the name "Foralkyl®" by the company Atochem; nonafluoromethoxybutane sold under the name "MSX 4518®" by the company 3M and nonafluoroethoxyisobutane; perfluoromorpholine derivatives, such as the 4-trifluoromethylperfluoromorpholine sold under the name "PF 5052®" by the company 3M;

silicone oils, such as volatile or non-volatile polymethylsiloxanes (PDMSs) containing a linear or cyclic silicone chain, that are liquid or pasty at room temperature, for exampleespecially cyclopolydimethylsiloxanes (cyclomethicones) such as cyclohexasiloxane; polydimethylsiloxanes comprising alkyl, alkoxy or phenyl groups, that are pendent or at the end of a silicone chain, wherein these groups contain from 2 to 24 carbon atoms; phenylsilicones, such as phenyltrimethicones, phenyldimethicones, phenyltrimethylsiloxydiphenylsiloxanes, diphenyldimethicones, diphenylmethyldiphenyltrisiloxanes, 2-phenylethyltrimethylsiloxysilicates and polymethylphenylsiloxanes;

mixtures thereof.

In the list of oils mentioned above, the expression "hydrocarbon-based oil" means any oil mainly comprising carbon and hydrogen atoms, and optionally ester, ether, fluoro, carboxylic acid and/or alcohol groups.

In the case where the cosmetic composition of the present disclosure is an emulsion, the oils, emulsifiers and coemulsifiers used may be chosen from those conventionally used in cosmetics or dermatology.

The emulsifier and optionally the coemulsifier may be present in the composition in a proportion ranging from 0.3% to 30% by weight, such as from 0.5% to 20% by weight, relative to the total weight of the composition.

The composition according to the invention may contain ionic or nonionic emulsifiers, the choice of which depends on the desired emulsion (W/O or O/W). Emulsifiers that may be used are those usually used in the field under consideration.

Emulsifiers that may be mentioned, for example, include nonionic surfactants such as fatty acid esters of polyols, and oxyalkylenated and oxyethylenated derivatives thereof; fatty acid ethers of polyols, and oxyalkylenated and, for example, oxyethylenated derivatives thereof, and mixtures thereof. When the emulsifiers are oxyalkylenated fatty acid esters of polyols or oxyalkylenated fatty alcohol ethers of polyols, there may be, for example, from 1 to 150 oxyalkylenated and especially oxyethylenated groups. Emulsifiers that may be mentioned include: a mixture of glyceryl stearate and PEG-100 stearate sold under the name ARLACEL 165 by the company ICI; polyoxyethylenated fatty alcohol ethers comprising from 1 to 100 oxyethylenated groups, such as, for example, ceteareth-1 2 and ceteareth-20, and mixtures thereof, such as the mixture sold under the name EMULGADE CM by the company Henkel (mixture of cetearyl isononanoate, ceteareth-20, cetearyl alcohol, glyceryl stearate, glycerol, ceteareth-12 and cetyl palmitate. The above emulsifiers are used for the preparation of oil/water emulsions.

Nonionic, anionic, amphoteric, or zwitterionic surfactants that promote the removal of makeup and impurities and which may make the composition foaming may also be added to the composition of this disclosure. For example, they may be foaming surfactants. Non-limiting examples of suitable foaming surfactants that may be used in the composition include:

(1) among nonionic surfactants, oxyethylenated oxypropylenated block polymers such as Poloxamer 184 (CTFA name); alkylpolyglycosides, such as alkylpolyglucosides (APG) having an alkyl group containing from 6 to 30 carbon atoms ($C_6$-$C_{30}$-alkyl polyglucosides), such as 8 to 16 carbon atoms, for example, decylglucoside ($C_9$/$C_{11}$-alkyl-polyglucoside (1.4)) such as the product sold under the name MYDOL 10 by the company Kao Chemicals, the product sold under the name PLANTAREN 2000 UP or PLANTACARE 2000 UP by the company Henkel, and the product sold under the name ORAMIX NS 10 by the company SEPPIC; caprylyl/capryl glucosides, such as the product sold under the name Oramix CG 110 by the company SEPPIC; laurylglucosides, such as the products sold under the names PLANTAREN 1200 N and PLANTACARE 1200 by the company Henkel; and cocoglucoside, for instance the product sold under the name PLANTACARE 818/UP by the company Henkel;

(2) among anionic surfactants, alkyl sulfates, alkyl ether sulfates and salts thereof, for instance the sodium salts thereof, such as the mixture of sodium laureth sulfate/magnesium laureth sulfate/sodium laureth-8 sulfate/magnesium laureth-8 sulfate, sold under the name TEXAPON ASV by the company Henkel; sodium lauryl ether sulfate (70/30 C12-14) (2.2 EO) sold under the names SIPON AOS 225 or Texapon N702 Paste by the company Henkel, ammonium lauryl ether sulfate (70/30 C12-C14) (3 EO) sold under the name SIPON-LEA 370 by the company Henkel; ammonium (C12-C14)alkyl ether (9 EO) sulfate sold under the name RHODAPEX AB/20 by the company Rhodia Chimie;

(3) among amphoteric or zwitterionic surfactants, alkylamido alkylamine derivatives such as N-disodium N-cocoyl-N-carboxymethoxyethyl-N-carboxymethylethylenediamine (CTFA name: disodium cocoamphodiacetate) sold as an aqueous saline solution under the name MIRANOL C2M CONC NP by the company Rhodia Chimie; N-sodium N-cocoyl-N-hydroxyethyl-N-carboxymethylethylenediamine (CTFA name: sodium cocamphoacetate) and the mixture of coconut acid ethanolamides (CTFA name: Cocoamide DEA).

The composition may also comprise a mixture of these surfactants.

The cosmetic composition may contain, besides water, one or more solvents chosen from lower alcohols containing from 1 to 6 carbon atoms, such as ethanol; polyols such as glycerol; glycols, for instance butylene glycol, isoprene glycol, hexylene glycol, propylene glycol or polyethylene glycols such as PEG-8; sorbitol; sugars such as glucose, fructose, maltose, lactose and sucrose; and mixtures thereof.

The composition used to impregnate the substrate may also comprise adjuvants conventionally used in the fields under consideration, such as organic solvents, solubilizing agents, hydrophilic or lipophilic thickeners, hydrophilic or lipphilic gelling agents, softeners, antioxidants, opacifiers, stabilizers, foaming agents, fillers, chelating agents, fragrances, screening agents, essential oils, dyestuffs, pigments, hydrophilic or lipophilic active agents, lipid vesicles optionally encapsulating one or more active agents, or any other ingredient conventionally used in cosmetics or dermatology.

The composition used to impregnate the substrate may also optionally contain preserving agents other than those mentioned above. The amounts of the various constituents of the compositions according to the present disclosure are those conventionally used in the fields under consideration.

Non-limiting examples of active agents that may be used include antiseborrhoeic active agents for cleaning the excess sebum on the skin, antimicrobial agents that remove from the skin any microorganisms that may be present thereon, and mixtures thereof.

Non-limiting examples of antiseborrhoeic active agents that may be used include sulfur and sulfur derivatives, benzoyl peroxide, zinc derivatives such as zinc sulfate and zinc oxide, aluminium chloride, selenium disulfide, B vitamins such as panthenol (vitamin B5) and niacinamide (vitamin B6 or PP), and mixtures thereof.

Non-limiting examples of active agents that may be used as antimicrobial agents include: β-lactam derivatives, quinolone derivatives, ciprofloxacin, norfloxacin, tetracycline and its salts (hydrochloride), erythromycin and its salts (zinc, estolate or stearate salt), amikacin and its salts (sulfate), 2,4,4'-trichloro-2'-hydroxydiphenyl ether (triclosan), 3,4,4'-trichlorobanilide (tricarban), phenoxyethanol, phenoxypropanol, phenoxyisopropanol, doxycycline and its salts (hydrochloride), capreomycin and its salts (sulfate), chlorhexidine and its salts (gluconate, hydrochloride), chlorotetracycline and its salts (hydrochloride), oxytetracycline and its salts (hydrochloride), clindamycin and its salts (hydrochloride), ethambutol and its salts (hydrochloride), hexamidine and its salts (isethionate), metronidazole and its salts (hydrochloride), pentamidine and its salts (hydrochloride), gentamicin and its salts (sulfate), kanamycin and its salts (sulfate), lineomycin and its salts (hydrochloride), methacycline and its salts (hydrochloride), methenamine and its salts (hippurate, mandelate), minocycline and its salts (hydrochloride), neomycin and its salts (sulfate), netilmicin and its salts (sulfate), paromomycin and its salts (sulfate), streptomycin and its salts (sulfate), tobramycin and its salts (sulfate), miconazole and its salts (hydrochloride), amanfadine and its salts (sulfate, hydrochloride), octopirox, para-ch loro-meta-xylenol, nystatin, tolnaftate, zinc pyrithione, clotrimazole, salicylic acid, 5-n-octanoylsalicylic acid (or capryloylsalicylic acid), benzoyl peroxide, 3-hydroxybenzoic acid, glycolic acid, lactic acid, 4-hydroxybenzoic acid, acetylsalicylic acid, 2-hydroxybutanoic acid, 2-hydroxypentanoic acid, 2-hydroxyhexanoic acid, phytic acid, N-acetyl-L-cysteine acid, lipoic acid, azelaic acid, arachidonic acid, ibuprofen, naproxen, hydrocortisone, acetaminophen, resorcinol, lidocaine hydrochloride, neomycin sulfate, octoxyglycerol, octanoylglycine (or capryloylglycine), caprylylglycol (1,2-octanediol) and 10-hydroxy-2-decanoic acid, and mixtures thereof.

In a non-limiting embodiment of the present disclosure, the microbial agents are chosen from 2,4,4'-trichloro-2'-hydroydiphenyl ether, 3,4,4'-trichlorobanilide, phenoxyethanol, phenoxypropanol, phenoxyisopropanol, chlorhexidine and its salts, octopirox, zinc pyrithione, salicylic acid, 5-n-octanoylsalicylic acid, benzoyl peroxide, 3-hydroxybenzoic acid, glycolic acid, lactic acid, 4-hydroxybenzoic acid, acetylsalicylic acid, 2-hydroxybutanoic acid, 2-hydroxypentanoic acid, 2-hydroxyhexanoic acid, phytic acid, N-acetyl-L-cysteine acid, lipoic acid, azelaic acid, arachidonic acid, octoxyglycerol, octanoylglycine, caprylyl glycol, 10-hydroxy-2-decanoic acid, and mixtures thereof.

Non-limiting examples of hydrophilic gelling agents that may be mentioned include carboxyvinyl polymers such as carbomers; modified acrylic copolymers such as acrylate/ alkylacrylate copolymers, such as the products sold under the name PEMULEN by the company Goodrich; polyacrylamides, for instance the product sold under the name Sepigel 305 by the company SEPPIC, or poly(2-acrylamido-2-methylpropanesulfonic acid) sold by the company Hoechst under the trade name HOSTACERIN AMPS (CFTA name: ammonium polyacryidimethyltauramide); polysaccharides, especially cellulose derivatives and natural gums, for instance xanthan gum or guar gum; and clays. Non limiting examples of lipophilic gelling agents that may be mentioned include modified clays such as bentones, metal salts of fatty-acids, hydrophobic silica, polyethylenes, and mixtures thereof. Additional gelling agents that may also be used include polymers with a hydrophobic function, such as polysaccharides with a hydrophobic chain, for instance quaternized guar gums.

The compositions according to the present disclosure are prepared according to the techniques that are well known to those skilled in the art of the field.

According to one non-limiting embodiment of the invention, the composition is in the form of a PIT (phase inverstion temperature) emulsion.

The principle of this technique for obtaining an oil/water emulsion is well known to those skilled in the art and is especially described in the articles "Phase Inversion Emulsification" by Th. Förster et al. published in Cosmetics & Toiletries, Vol.106, December 1991, pp. 49-52, "Application of the phase-inversion-temperature method to the emulsification of cosmetics" by T. Mitsui et al. published in American Cosmetics and Perfumery, vol. 87, December 1972.

The PIT technique gives "ultrafine" oil/water emulsions, wherein the mean size of the globules constituting the fatty phase is within well-defined limits, i.e., between 50 and 1000 nm. These emulsions are extremely fluid and are particularly suitable for impregnating water-insoluble substrates so as to constitute cleansing articles or wipes.

According to one non-limiting embodiment of the present disclosure, the PIT emulsion is prepared in concentrated form and then diluted, generally just before impregnation, with one to nine parts of an aqueous phase that may also contain all or some of the predissolved preserving agents.

The viscosity of the cosmetic composition used in the article according to the present disclosure is, for example, less than 1500 and may be less than 1000 mPa.s. The viscosity is measured at room temperature (about 25° C.) using a Rheomat RM 180 machine.

The cosmetic article according to the present disclosure may be configured in the form of a wipe, a compress, a glove, a mitten, a slipper, a fingerstall, a bonnet, a skullcap, or a mask in the form of all or part of the face. In the latter case, the mask may be designed for the whole face or specifically for the top or bottom of the face only.

In a non-limiting embodiment of the present disclosure, when the cosmetic article of the present invention is configured as a glove or a fingerstall that is to be used to treat an area of the body (skin or hair) other than the hand, the face having the higher hydrophilicity may be positioned to the exterior of the article, as the surface serving to deposit the impregnated product.

In another non-limiting embodiment of the present disclosure, the article may be configured in the form of a glove, a fingerstall or a slipper that is used to treat all or part of the hand or the foot, such as in the case of the application of a softening, moisturizing or stain-removing treatment. In this case, the more hydrophilic surface will be on the inside of the glove or slipper.

Further, in another non-limiting embodiment of the present disclosure, if the article is configured as a skullcap, a bonnet or a headcap, the face having the higher hydrophilicity will advantageously be positioned to the inside of the article, as a surface serving to deposit the impregnated product.

Finally, in another non-limiting embodiment of the present disclosure, when the article is configured in the form of an impregnated mask for facial care, the face of the support having the higher hydrophilicity will advantageously be positioned next to the face.

The cosmetic composition used in the article according to the present disclosure may be a hair composition, such as a composition for cleansing or coloring/bleaching the hair, or a composition for the skin or mucous membranes thereof, such as a care composition, a self-tanning composition, a makeup-removing composition, a scrubbing composition or a coloring composition.

According to another aspect of the present disclosure, a single-use cosmetic article comprising at least one substrate impregnated with a liquid cosmetic composition is formed, wherein the substrate is permeable and comprises at least first and second groups of fibers, wherein the second group of fibers has a hydrophilicity that is different from that of the first group of fibers, the first and second groups of fibers being arranged within the same layer of the substrate, such that a first face of the substrate, which is to the outside of this substrate, has a hydrophilicity higher than the hydrophilicity of a second face of the substrate, opposite the first face, the article comprising at least one hollow or concave portion, the hollow or concave portion being configured:
  i) either to receive a surface to be treated so as to bring the surface into contact with an inner surface of the article;
  ii) or to receive all or part of a hand, so as to bring an outer surface of the article into engagement with a surface to be treated.

The above hollow or concave article may be configured in the form of a glove, a mitten, a slipper, a fingerstall, a bonnet, a skullcap or a headcap.

The hollow article may be obtained by assembling at least "two sheets" along their respective edges, or by folding a sheet on itself and then fixing on themselves the edges of the sheet thus folded.

When the hollow or concave portion is configured to receive all or part of a hand, in order to bring an outer surface of the article into engagement with a surface to be treated, the more hydrophilic face is on the outside of the hollow or concave portion.

Conversely, when the hollow or concave portion is configured (i.e as a glove, a mitten, a slipper, a fingferstall, a bonnet, a skullcap, or a headcap), to receive a surface to be treated, the more hydrophilic face is on the inside of the hollow or concave portion.

In one non-limiting embodiment, the substrate is a monolayer substrate.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific example are reported as precisely as possible. Any numerical value, however, inherently contain certain errors necessarily resulting from the standard deviation found in their respective testing measurements.

The following examples are intended to illustrate the invention in a non-limiting manner.

EXAMPLES

Example 1

Hair-Cleansing Glove

The cleansing composition described below was impregnated to 200% onto a Sandler nonwoven ref. 03/02/1001.

| Ingredients: | % by mass: |
|---|---|
| WATER | qs 100 |
| DENATURED ALCOHOL (93.1%)/AQUA | 20% |
| DISODIUM COCOAMPHODIACETATE | 0.15% |
| HYDROGENATED POLYISOBUTENE | 5% |
| FRAGRANCE | 0.2% |

The Sandler nonwoven ref. 03/02/1001 was obtained by hydrobonding and was composed of 100% of viscose fibers on one face and of 100% of polypropylene (PP) fibers on the other face. It was cut into the shape of a mitten or a glove, the PP faces of which were welded internally via the edges so as to form a bag into which the hand may be introduced.

The presence of PP fibers made it possible to weld the glove, and on account of their hydrophobic nature, made it possible for the hand to either not come into contact with or to minimally contact the fluid impregnated on the substrate.

The presence of viscose fibers on the outside of the glove allowed good impregnation of the fluid and optimum release of the lotion onto the surface to be cleansed (skin or hair).

For the article formed according to this example, the ratio RISP1/RISP2 was 8.4.

Example 2

Mechanical Exfoliation/Chemical Peeling Wipe

The exfoliant composition described below was impregnated to 300% onto a Jacob Holm nonwoven ref. Rough & Soft 107103/003A.

| Ingredients: | % by mass: |
|---|---|
| WATER | qs 100 |
| DENATURED ALCOHOL (93.1%)/AQUA | 5% |
| GLYCEROL | 3% |
| PRESERVING AGENTS | 0.5% |
| GLYCOLIC ACID | 1% |
| FRAGRANCE | 0.2% |

The Jacob Holm nonwoven ref. Rough & Soft 107103/003A was obtained by hydrobonding, and was composed of 100% of a mixture of viscose and terephthalate polyester fibers on one face, 100% of polypropylene (PP) fibers on the other face.

These PP fibers gave the face over the substrate a rough nature suitable for mechanical exfoliation during the passage of this face of the skin. The impregnated exfoliating composition was then applied by passing the other soft, hydrophilic face over the skin.

For the article formed according to this example, the ratio RISP1/RISP2 was 1.75.

Example 3

Mechanical Exfoliation/Soothing Lotion Wipe

The soothing composition described below was impregnated to 300% onto a PGI Duralace 7163, 80 gsm Cartex Blue nonwoven.

| Ingredients: | % by mass: |
|---|---|
| WATER | qs 100 |
| ALLANTOIN | 0.15% |
| GLYCEROL | 5% |
| PEG-8 | 3% |
| PRESERVING AGENTS | 0.3% |
| POTASSIUM GLYCYRRHETINATE | 0.1 |
| FRAGRANCE | 0.1% |

The PGI Duralace 7163, 80 gsm Cartex Blue nonwoven was obtained by hydrobonding, and was composed of 100% of a mixture of viscose and terephthalate polyester fibers on one face, and 100% high-denier polypropylene (PP) fibers on the other face.

The PP fibers gave the face of the substrate a rough nature suitable for mechanical exfoliation during the passage of this face over the skin. The impregnated soothing composition was then applied by passing the other soft and hydrophilic face over the skin.

The wipe according to this example may also be used as a mask by leaving it placed on the face, with the soft, hydrophilic face against the face.

For the article formed according to this example, the ratio RISP1/RISP2 was 2.1.

Example 4

Makeup-Removing Wipe

The makeup-removing composition described below was impregnated to 300% onto a Sandler nonwoven ref. 03/02/1001.

| Ingredients: | % by mass: |
|---|---|
| WATER | qs 100 |
| XANTHAN GUM | 0.1% |
| GLYCERYL STEARATE | 0.25% |
| ISOPROPYL PALMITATE | 1% |
| CETYL ALCOHOL | 0.15% |
| GLYCEROL | 3% |
| PRESERVING AGENTS | 0.45% |
| GLYCINE SOYBEAN OIL | 0.05% |
| PEG-100 STEARATE | 0.25% |
| FRAGRANCE | 0.05% |
| PRUNUS AMYGDALUS DULCIS (SWEET ALMOND) | 1.2% |
| OILPRUNUS AMYGDALUS DULCIS (SWEET ALMOND) | 1.2% |

The Sandler nonwoven ref. 03/02/1001 was obtained by hydrobonding, and was composed of 100% viscose fibers on one face and 100% polypropylene (PP) fibers on the other face.

The presence of viscose fibers on a first face of the substrate allowed good impregnation of the fluid and optimum release of the makeup-removing composition, thus improving makeup removal.

The presence of PP fibers on the second face of the substrate allowed minimum release of the makeup-removing composition via this face, which may be used to remove residual makeup remover.

For the article formed according to this example, the ratio RISP1/RISP2 was 2.65.

Example 5

Exfoliant/Makeup-Removing Wipe

The makeup-removing composition described below was impregnated to 300% onto a Jacob Holm nonwoven ref. Rough & Soft 107103/003A.

| Ingredients: | % by mass: |
|---|---|
| WATER | qs 100 |
| DICAPRYLYL ETHER | 3% |
| EHTYLHEXYL PALMITATE | 3% |
| CETEARYL ALCOHOL | 0.31% |
| CETEARETH-12 | 0.62% |
| CETEARETH-20 | 1.52% |
| PEG-4 DILAURATE | 0.08% |
| GLYCEROL | 5% |
| MINERAL OIL | 5% |
| PRESERVING AGENTS | 0.15% |
| FRAGRANCE | 0.3% |

The Jacob Holm nonwoven ref. Rough & Soft 1071 03/003A was obtained by hydrobonding and was composed of 100% of a mixture of viscose and terephthalate polyester fibers on one face and 100% of polypropylene (PP) fibers on the other face.

The makeup-removing lotion was first applied by passing the soft and hydrophilic face over the skin, allowing optimum release and thus better makeup-removing efficacy. The polypropylene fibers gave the less hydrophilic face of the substrate a rough nature suitable for gentle exfoliation to clean deep-down.

For the article formed according to this example, the ratio RISP1/RISP2 is 4.

Example 6

Self-Tanning Wipe

The self-tanning composition described below was impregnated to 400% onto a Jacob Holm nonwoven ref. Rough & Soft 1071 03/003A.

| Ingredients: | % by mass: |
|---|---|
| WATER | qs 100 |
| DIHYDROXYACETONE | 5% |
| PRESERVING AGENTS | 0.5% |
| PROPYLENE GLYCOL | 25% |
| BEHENETH 10 | 2.5% |

-continued

| Ingredients: | % by mass: |
|---|---|
| CYCLOPENTASILOXANE | 15% |
| LAURETH-4 | 2.5% |
| ISOPROPYL MYRISTATE | 6% |

The Jacob Holm nonwoven ref. Rough & Soft 1071 03/003A was obtained by hydrobonding, and was composed of 100% of a mixture of viscose and terephthalate polyester fibers on one face and 100% high-denier polypropylene (PP) fibers on the other face.

The PP fibers gave the face of the substrate a rough nature suitable for mechanical exfoliation when this face is passed over the skin. This exfoliation made it possible to remove dead cells and to prepare the skin in a certain manner. The self-tanning lotion was then applied by passing the other, soft and hydrophilic face over the skin.

For the article formed according to this example, the ratio RISP1/RISP2 was 2.93.

Example 7

Care Mask

The care composition described below was impregnated to 600% onto a Sandier nonwoven ref. 03/02/1001.

| Ingredients: | % by mass: |
|---|---|
| WATER | qs 100 |
| XANTHAN GUM | 0.15% |
| SODIUM MYRISTOYL GLUTAMATE | 0.05% |
| CYCLOPENTASILOXANE | 0.4% |
| PRESERVING AGENTS | 0.2% |
| BUTYLENE GLYCOL | 10% |
| GLYCEROL | 3% |
| FRAGRANCE | 0.2% |

The Sandier nonwoven ref. 03/02/1001 was obtained by hydrobonding, and was composed of 100% of viscose fibers on one face and 100% polypropylene (PP) fibers on the other face.

The presence of viscose fibers on the outside of the mask made it possible to concentrate the majority of the care composition on this face and to release it onto the face in an optimum manner. As a result, the mask may be impregnated with a smaller amount of care composition, while at the same time obtaining an effect that is just as good. One or the other of the faces may be printed on or made from colored fibers so as to clearly discern the face to be applied to the face.

For the article formed according to this example, the ratio RISP1/RISP2 was 1.75.

What is claimed is:

1. A cosmetic article comprising a substrate impregnated with an aqueous liquid cosmetic composition, said substrate being permeable and comprising at least a first group of fibers and at least a second group of fibers whose hydrophilicity is different from that of the fibers of the first group, wherein:

the first and second groups of fibers are present within the same layer of the substrate and are arranged such that a first face of the substrate has a hydrophilicity substantially greater than the hydrophilicity of a second face of the substrate, opposite the first face, the first face being external to the substrate, the first face of the substrate has a release index under static pressure (RISP1),
the second face of the substrate has a release index under static pressure (RISP2), and
the ratio RISP1/RISP2 is greater than or equal to 1.5.

2. The cosmetic article of claim 1, wherein the substrate is a monolayer substrate.

3. The cosmetic article of claim 1, wherein the ratio RISP1/RISP2 ranges from 1.5 to 15.

4. The cosmetic article of claim 3, wherein the ratio RISP1/RISP2 ranges from 2.5 to 7.

5. The cosmetic article of claim 1, wherein the substrate is obtained by hydrobonding of a first web of the fibers of the first group and of a second web of said fibers of the second group.

6. The cosmetic article of claim 1, wherein the substrate is impregnated with from 100% to 1000% by weight of said liquid cosmetic composition relative to the weight of the substrate prior to impregnation.

7. The cosmetic article of claim 6, wherein the substrate is impregnated with from 150% to 400% by weight of said liquid cosmetic composition relative to the weight of the substrate prior to impregnation.

8. The cosmetic article of claim 1, wherein the liquid cosmetic composition comprises from 10% to 99.9% of water.

9. The cosmetic article of claim 1, wherein the liquid cosmetic composition comprises from 30% to 90% of water.

10. The cosmetic article of claim 1, wherein the liquid cosmetic composition comprises a fatty phase.

11. The cosmetic article of claim 10, wherein the cosmetic composition comprises from 0.5% to 80% by weight of the fatty phase by weight relative to the total weight of the cosmetic composition.

12. The cosmetic article of claim 11, wherein the cosmetic composition comprises from 1% to 50% by weight of the fatty phase by weight relative to the total weight of the cosmetic composition.

13. The cosmetic article of claim 10, wherein the fatty phase is chosen from hydrocarbon-based oils of animal origin, hydrocarbon-based oils of plant origin, synthetic esters and synthetic ethers, linear or branched hydrocarbons of mineral or synthetic origin, fatty alcohols containing from 8 to 26 carbon atoms, alkoxylated fatty alcohols, partially hydrocarbon-based and/or silicone-based fluoro oils, silicone oils, and mixtures thereof.

14. The cosmetic article of claim 1, wherein the cosmetic composition further comprises at least one compound chosen from organic solvents, solubilizers, hydrophilic or lipophilic thickeners, hydrophilic or lipophilic gelling agents, softeners, antioxidants, opacifiers, stabilizers, foaming agents, fillers, chelating agents, fragrances, screening agents, essential oils, dyestuffs, pigments, hydrophilic or lipophilic active agents, and lipid vesicles optionally encapsulating one or more active agents.

15. The cosmetic article of claim 1, wherein the cosmetic composition further comprises at least one solvent chosen from lower alcohols containing from 1 to 6 carbon atoms; polyols; glycols; sorbitol; sugars; and mixtures thereof.

16. The cosmetic article of claim 1, wherein the cosmetic composition has a viscosity of less than 1500 mPa.s.

17. The cosmetic article of claim 16, wherein the cosmetic composition has a viscosity of less than 1000 mPas.

18. The cosmetic article of claim 1, wherein the fibers of the first group are selected from cotton, cellulose and viscose fibers.

19. The cosmetic article of claim 1, wherein the fibers of the second group are chosen from polypropylene, polyester, polyamide and polyethylene fibers.

20. The cosmetic article of claim 1, wherein one of the faces of the substrate is rendered exfoliant.

21. The cosmetic article of claim 20, wherein the second face of the substrate is rendered exfoliant.

22. The cosmetic article of claim 1, wherein the article is configured in the form of a wipe, a compress, a glove, a mitten, a fingerstall, a slipper, a bonnet, a skullcap or a mask in the form of all or part of the face.

23. The cosmetic article of claim 1, wherein the cosmetic composition is chosen from a hair composition, a composition for the skin or mucous membranes, a self-tanning composition, a makeup-removing composition, a desquamating composition or a coloring composition.

24. A cosmetic article comprising at least one substrate impregnated with a liquid cosmetic composition, said substrate being permeable and comprising at least a first group of fibers and at least a second group of fibers whose hydrophilicity is different from that of the fibers of the first group, wherein the first and second groups of fibers are present within the same layer of the substrate and arranged such that a first face of the substrate, which is to the outside of this substrate, has a hydrophilicity higher than the hydrophilicity of a second face of the substrate, opposite the first face, said cosmetic article further comprising at least one hollow or concave portion, said hollow or concave portion being configured so as to:
  i) receive a surface to be treated; or
  ii) to receive all or part of a hand in order to bring the article into engagement with a surface to be treated:
and wherein:
the first face of the substrate has a release index under static pressure (RISP1),
the second face of the substrate has a release index under static pressure (RISP2), and
the ratio RISP1/RISP2 is greater than or equal to 1.5.

25. The cosmetic article of claim 24, wherein the article is configured in the form of a glove, a mitten, a fingerstall, a slipper, a bonnet, a skullcap or a headcap.

26. The cosmetic article of claim 24, wherein the hollow or concave portion is configured so as to receive all or part of a hand in order to bring the article into engagement with a surface to be treated, said first face being on the outside of the hollow or-concave portion.

27. The cosmetic article of claim 18, wherein the hollow or concave portion is configured so as to receive a surface to be treated, said first face being on the inside of the hollow or concave portion.

28. The cosmetic article of claim 18, wherein the substrate is a monolayer substrate.

* * * * *

UNITED STATES PATENT AND TRADEMARK OFFICE
CERTIFICATE OF CORRECTION

PATENT NO.          : 7,514,071 B2                                                      Page 1 of 1
APPLICATION NO. : 11/074056
DATED               : April 7, 2009
INVENTOR(S)         : Pascal Simon et al.

It is certified that error appears in the above-identified patent and that said Letters Patent is hereby corrected as shown below:

In claim 16, column 15, line 60, "mPa.s." should read --mPa·s.--.

In claim 17, column 16, line 2, "mPas." should read --mPa·s.--.

In claim 22, column 16, line 15, "mitten,a" should read --mitten, a--.

In claim 24, column 16, line 38, "treated:" should read --treated;--.

In claim 24, column 16, line 43, "(RISP2),and" should read --(RISP2), and--.

In claim 26, column 16, line 52, "or-concave" should read --or concave--.

Signed and Sealed this

Nineteenth Day of May, 2009

JOHN DOLL
*Acting Director of the United States Patent and Trademark Office*